United States Patent
Fujii et al.

(10) Patent No.: US 9,545,102 B2
(45) Date of Patent: Jan. 17, 2017

(54) SUSTAINED RELEASE PHEROMONE PREPARATION TARGETING INSECT PEST HAVING CARBOXYLIC ACID AS PHEROMONE SUBSTANCE

(75) Inventors: Tatsuya Fujii, Joetsu (JP); Tatsuya Hojo, Joetsu (JP); Naoki Ishibashi, Joetsu (JP); Ryuichi Saguchi, Joetsu (JP); Takehiko Fukumoto, Joetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 13/325,838

(22) Filed: Dec. 14, 2011

(65) Prior Publication Data

US 2012/0156165 A1 Jun. 21, 2012

(30) Foreign Application Priority Data

Dec. 17, 2010 (JP) ................................. 2010-281579

(51) Int. Cl.
*A01N 25/10* (2006.01)
*A01N 37/02* (2006.01)
*A01N 25/18* (2006.01)

(52) U.S. Cl.
CPC .................................... *A01N 25/18* (2013.01)

(58) Field of Classification Search
CPC ......... A01N 25/10; A01N 25/12; A01N 37/02
See application file for complete search history.

(56) References Cited

U.S. PATENT DOCUMENTS

| | | | |
|---|---|---|---|
| 6,562,331 B1 * | 5/2003 | Ito et al. | 424/84 |
| 2003/0198659 A1 * | 10/2003 | Hoffmann et al. | 424/411 |
| 2012/0282214 A1 * | 11/2012 | Matsuura et al. | 424/84 |

FOREIGN PATENT DOCUMENTS

| | | | |
|---|---|---|---|
| EP | 0194934 A1 | 9/1986 | |
| JP | 57-009705 A | 1/1982 | |
| JP | 57-031638 A | 2/1982 | |
| JP | 03-118301 A | 5/1991 | |
| JP | 06-211614 | * 8/1994 | |
| JP | 06-211614 A | 8/1994 | |
| JP | 09132507 A | * 5/1997 | ............ A01N 63/00 |
| JP | 11-069936 A | 3/1999 | |
| JP | 11-279011 A | 10/1999 | |
| JP | 2001-513789 T | 9/2001 | |

OTHER PUBLICATIONS

Megatomoic acid (http://www.pherobase.com/database/synthesis/synthesis-detail-megatomoic%20acid.php (downloaded on Jul. 30, 2013)).*
Joshua Rodstein et al. Identification and Synthesis of a Female-Porduced Sex Pheromone forthe Cerambycid Beetle Prionus californicus, J. Chem. Ecol. 35, 590-600, 2009.*
Japanese Office Action for Application No. 2010-281579, dated Apr. 9, 2013.

* cited by examiner

*Primary Examiner* — Michael G Hartley
*Assistant Examiner* — Jagadishwar Samala
(74) *Attorney, Agent, or Firm* — Alston & Bird LLP

(57) ABSTRACT

Targeting an insect pest having a carboxylic acid compound as a pheromone substance, provided is a sustained release pheromone preparation enabling a high amount of pheromone to be released during the control period. More specifically, provided is a sustained release pheromone preparation, comprising: a carboxylic acid compound to be released, and an ethylene-vinyl acetate copolymer membrane through which the carboxylic acid compound can permeate, wherein the preparation is targeted for an insect pest having the carboxylic acid compound as a pheromone substance.

4 Claims, No Drawings

SUSTAINED RELEASE PHEROMONE PREPARATION TARGETING INSECT PEST HAVING CARBOXYLIC ACID AS PHEROMONE SUBSTANCE

CROSS-REFERENCE TO RELATED APPLICATIONS

This application claims priority from Japanese Patent Application No. 2010-281579, filed Dec. 17, 2010, the disclosure of which is incorporated by reference herein in its entirety.

BACKGROUND OF THE INVENTION

1. Field of the Invention

The present invention relates to a sustained release pheromone preparation which releases a sex pheromone substance into air to control an insect pest having a carboxylic acid compound as a pheromone substance by mass trapping or mating disruption.

2. Description of the Related Art

It is important for establishing a control technology with pheromone to sustainedly release a sufficient amount of pheromone from an attraction source to attract wild insect pests with respect to the mass trapping, and to maintain a sufficient amount of pheromone to cause mating disruption in an entire region to be controlled with respect to the mating disruption. Because an insect pest generally emerges over a long period of time, typically from spring to autumn, sustained release of a pheromone substance from a sustained release pheromone preparation comprising the pheromone substance makes the mass trapping or the mating disruption possible over the entire period of emergence. Thus, to establish a pheromone-based control technology, development of a sustained release pheromone preparation for the insect pests to be controlled is very important.

In order to release a constant amount of an active component over a long period time, a sustained pheromone preparation is in form of a sealed container, wherein the container includes a cap, a small tube, a laminate envelope and a capsule and is made of a material having an ability to control a release amount. The material includes rubber, polyethylene, polypropylene, an ethylene-vinyl acetate copolymer containing 90% by weight or greater of ethylene repeating units, and polyvinyl chloride (JP 11-069936A). Among them, polyolefin-based plastics, which typically include polyethylene, are available in various grades with different properties so that they come in a broad range of selection as a material. The polyolefin-based plastics are also widely used so that they are inexpensive. Further, the polyolefin-based plastics excel in moldability and can be molded in various ways such as extrusion molding, film molding, stretch molding and injection molding. The polyolefin-based plastics excel in mechanical strength, particularly in mechanical strength at low temperature so that they can be suitably used during a time of low temperature period or in a low temperature region. Moreover, aldehyde or acetate compounds, which are contained by most of the pheromone substances for the insect pests in Lepidoptera, can be comprised by a sustained release pheromone preparation with a polyethylene membrane and result in a control effect (JP 57-009705A).

BRIEF SUMMARY OF THE INVENTION

The present inventors have found that a highly polar material such as a carboxylic acid compound is hardly released from a plastic container with a polyethylene membrane. However, it is necessary to maintain a high release amount from a sustained release pheromone preparation in order to make the mass trapping or the mating disruption possible. Thus, a sustained release pheromone preparation for an insect pest having a carboxylic acid compound as a pheromone substance is desired. The present invention is to provide a pheromone preparation for controlling an insect pest having a carboxylic acid compound as a pheromone substance, wherein the preparation can provide a high release amount of pheromone during a control period.

The present inventors initially believed that the carboxylic acid compound might form a dimer through hydrogen bonding or an anhydride through dehydration to result in a higher boiling point so that the permeability of the polyethylene membrane was lowered. However, as a result of more extensive studies, they have found that the difference in permeability is due to the fact that the aldehyde or acetate compound has good compatibility or affinity with a polyethylene membrane, while a carboxylic acid compound has very poor compatibility or affinity with a polyethylene membrane. The present inventors have found that use of an ethylene-vinyl acetate copolymer (hereinafter described also as "EVA"), especially EVA having high content of vinyl acetate repeating units, results in constant release of the carboxylic acid compound for a long period of time. Thus, the invention has been completed.

The invention provides a sustained release pheromone preparation, comprising a carboxylic acid compound to be released and an ethylene-vinyl acetate copolymer membrane through which the carboxylic acid compound can permeate, wherein the preparation is targeted for an insect pest having a carboxylic acid compound as a pheromone substance.

According to the sustained release pheromone preparation of the invention, the preparation can control an insect pest having a carboxylic acid compound as a pheromone substance.

DETAILED DESCRIPTION OF THE INVENTION

The subject to be controlled by the sustained release pheromone preparation of the invention is not particularly limited as long as an insect pest has a carboxylic acid compound as a pheromone substance. Examples of the insect pest include insects in Lepidoptera, Cleoptera and Hymenoptera. Specific examples thereof include California prionus (*Prionus carifonicus*), *Anthrenus verbasci* and *Attagenus unicolor*.

The carboxylic acid compound which is comprised by and released from the sustained release pheromone preparation is a pheromone substance of an insect pest to be controlled. The carboxylic acid compound as a pheromone substance is not particularly limited as long as it is a compound having a carboxylic group. Examples thereof include a compound having two or more methyl groups and/or a double bond in a carbon skeleton. Specific examples thereof include 3,5-dimethyl dodecanoic acid, Z-5-undecenoic acid, E-5-undecenoic acid and (E, Z)-3,5-tetradecadienoic acid.

The sustained release pheromone preparation comprises an EVA membrane through which the carboxylic acid compound can permeate. From the viewpoint of releasability and processability, the content of the vinyl acetate repeating units in the EVA copolymer is preferably 4 to 20% by weight, particularly preferably 10 to 15% by weight. The content of the ethylene repeating units in the EVA copolymer is preferably 80 to 96% by weight, particularly preferably 85 to 90% by weight. It should be noted that the content of the vinyl acetate repeating units means the content of the repeating units derived from vinyl acetate in the copolymer.

When the vinyl acetate content is less than 4% by weight, the permeation rate of the pheromone substance through the membrane may be slow even when the EVA membrane is kept thin. As a result, it may not be possible to obtain a suitable release rate. When the vinyl acetate content is more than 20% by weight, rigidity of the polymer itself may be weakened so that it may not be possible to transform the polymer into a preparation.

The molecular weight of the EVA is not particularly limited. From the viewpoint of releasability and processability, the weight average molecular weight (Mw) of the EVA measured with the gel permeation chromatography (GPC) is preferably 50,000 to 500,000 by using polystyrene as a standard.

When EVA having a carboxylic acid compound permeability is made into a membrane of a sustained release pheromone preparation, the carboxylic acid compound can be slowly released through the membrane to the outside such as a field or a farm. The EVA membrane may be the whole of the container of a sustained release pheromone preparation or a part of the container such as a wall of the container. When only a part of the container is made of an EVA membrane, the carboxylic acid compound can be released through the EVA membrane. When the other part of the container is made of, for example, a polyethylene membrane, a pheromone substance other than the carboxylic acid compound can be also released simultaneously.

The pheromone substance compound other than the carboxylic acid compound which can be used in combination of the carboxylic acid is not particularly limited as long as it does not have high reactivity or high degradability in the presence of the carboxylic acid. Examples thereof include an aldehyde compound, an acetate compound, an alcohol compound, a ketone compound and a hydrocarbon compound.

A form of the preparation in which the carboxylic acid compound is enclosed is preferably a pheromone preparation form enabling the compound to permeate through a membrane. Examples thereof include a tube, a capsule, an ampoule and a bag. The filling amount in each preparation is preferably 30 to 1000 mg, more preferably 50 to 500 mg. From the viewpoint of constant releasability, in particular, the tube type preparation preferably has an inner diameter of 0.5 to 2.5 mm, surface area of 600 to 4000 $mm^2$ and membrane thickness of 0.20 to 0.75 mm.

From the viewpoint of preventing UV-caused deterioration of the carboxylic acid compound, an inorganic colorant such as iron oxide, chrome oxide, titanium oxide and carbon black, or an organic colorant such as a polycyclic pigment and an azo-based pigment may be added preferably in the total amount of 3% by weight or less, more preferably 1% by weight or less based on the weight of the carboxylic acid compound.

Further, a stabilizing agent such as an antioxidant and an ultraviolet absorbent can be added to prevent deterioration of the polymer during use. The antioxidant includes a phenol-based anti-oxidant, a sulfur-based anti-oxidant and a phosphorus-based anti-oxidant. The ultraviolet absorbent includes a benzotriazole-based ultraviolet absorbent and a benzophenone-based ultraviolet absorbent. Moreover, an antiblocking agent or a lubricant can be added to improve processability. The antiblocking agent includes a metal salt of higher fatty acid and an inorganic powder. The lubricant includes hydrocarbon, alcohol, higher fatty acid, ester, a partial ester of polyhydric alcohol, a metal salt of higher fatty acid, natural wax, fatty acid amide and a polymer.

The sustained release pheromone preparation can be prepared by placing a liquid pheromone substance in a container which has been formed by blow molding or extrusion molding, and sealing the container. According to circumstances, a container may be filled with a liquid pheromone substance by using the same route as the route through which air is extruded during molding, and sealed.

EXAMPLES

Examples and Comparative Examples of the invention are described in detail below. It should not be construed that the invention is limited by the Examples.

Example 1 to 6 and Comparative Example 1

Tubing being made of ethylene-vinyl acetate copolymer containing 4% by weight of vinyl acetate repeating units and having an inner diameter of 0.6 mm and a thickness (membrane thickness) of 0.2 mm was produced by extrusion molding at a temperature of 150 to 200° C. in Example 1. Provided was a mixture containing 50 mg of 3,5-dimethyl-dodecanoic acid and 2% by weight DBH (5-di-tert-butyl-hydroquinone) and 2% by weight HBMCBT (2-(2'-hydroxy-3'-t-butyl-5'-methylphenyl)-5-chlorobenzotriazole), wherein the DBH and HBMCBT were stabilizing agents. The mixture was injected from one end of the tubing and then both ends were sealed by applying pressure to them under high frequency heating. Subsequently, by cutting at the welded part, a sustained release pheromone preparation with a length of 20 cm was prepared.

In addition, a sustained release pheromone preparation was prepared in the same manner as described above by using tubing having an inner diameter of 0.6 mm and a membrane thickness of 0.2 mm produced by extrusion molding of the EVA having 10% of vinyl acetate repeating units in Example 2, 15% by weight of vinyl acetate repeating units in Example 3, or 20% by weight of vinyl acetate repeating units in Example 6, tubing having an inner diameter of 0.6 mm and a membrane thickness of 0.4 mm produced by extrusion molding of the EVA having 15% by weight of vinyl acetate repeating units in Example 4, or tubing having an inner diameter of 0.6 mm and a membrane thickness of 0.6 mm produced by extrusion molding of the EVA having 15% by weight of vinyl acetate repeating units in Example 5.

Further, a sustained release pheromone preparation was prepared in the same manner as described above by using tubing having an inner diameter of 0.6 mm and a membrane thickness of 0.2 mm produced by extrusion molding of high density polyethylene (HDPE) in Comparative example 1.

Each preparation was stored in a constant temperature vessel of 30° C. and a wind rate of 0.3 m, and the release rate was measured for each preparation for a period of 120 days.

TABLE 1

| | inner diameter of tube (mm) | thickness of tube membrane (mm) | content of vinyl acetate repeating units (% by weight) |
|---|---|---|---|
| Example 1 | 0.6 | 0.2 | 4 |
| Example 2 | 0.6 | 0.2 | 10 |
| Example 3 | 0.6 | 0.2 | 15 |
| Example 4 | 0.6 | 0.4 | 15 |

TABLE 1-continued

| | inner diameter of tube (mm) | thickness of tube membrane (mm) | content of vinyl acetate repeating units (% by weight) |
|---|---|---|---|
| Example 5 | 0.6 | 0.6 | 15 |
| Example 6 | 0.6 | 0.2 | 20 |
| Comp. Ex. 1 | 0.6 | 0.2 | 0 |

TABLE 2

| | release rate (mg/day/preparation) | | | |
|---|---|---|---|---|
| | after 30 days | after 60 days | after 90 days | after 120 days |
| Example 1 | 0.23 | 0.23 | 0.25 | 0.21 |
| Example 2 | 0.36 | 0.27 | 0.32 | 0.29 |
| Example 3 | 0.41 | 0.37 | 0.41 | 0.38 |
| Example 4 | 0.18 | 0.27 | 0.30 | 0.28 |
| Example 5 | 0.15 | 0.23 | 0.25 | 0.21 |
| Example 6 | 0.53 | 0.47 | 0.50 | 0.47 |
| Comp. Ex. 1 | 0.05 | 0.08 | 0.08 | 0.06 |

The sustained release pheromone preparation comprising, as a membrane material, the high density polyethylene having 0% by weight of vinyl acetate repeating units, hardly released 3,5-dimethyldodecanoic acid. However, the release rate increased as the content of vinyl acetate repeating units increased. It is believed that the carboxylic acid compound cannot easily permeate through polyethylene so that a release amount from the preparation is low, while the carboxylic acid compound can easily permeate through an EVA preparation membrane having vinyl acetate repeating units mixed so that a release amount from the preparation becomes high.

The invention claimed is:

1. A sustained release pheromone preparation, comprising:
   a container;
   a carboxylic acid compound in the container to be sustainedly released to the outside of the container, said carboxylic acid compound is selected from the group consisting of 3,5-dimethyl dodecanoic acid, Z-5-undecenoic acid, and E-5-undecenoic acid; and
   an ethylene-vinyl acetate copolymer membrane which comprises at least part of the container, through which the carboxylic acid compound can permeate,
   wherein the preparation is targeted for an insect pest having said carboxylic acid compound as a pheromone substance.

2. The sustained release pheromone preparation according to claim 1, wherein the ethylene-vinyl acetate copolymer contains 4 to 20% by weight of vinyl acetate repeating units.

3. The sustained release pheromone preparation according to claim 1, wherein the preparation is in form of a capsule, an ampoule or a bottle.

4. The sustained release pheromone preparation according to claim 2, wherein the preparation is in form of a capsule, an ampoule or a bottle.

* * * * *